United States Patent
Ueda et al.

(10) Patent No.: US 12,011,448 B2
(45) Date of Patent: Jun. 18, 2024

(54) THERAPEUTIC OR PREVENTING AGENT FOR NEPHROTIC SYNDROME INCLUDING INDOLE COMPOUND

(71) Applicant: Japan Tobacco Inc., Tokyo (JP)

(72) Inventors: Yoshifumi Ueda, Takatsuki (JP); Takafumi Kurimoto, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 853 days.

(21) Appl. No.: 17/056,931

(22) PCT Filed: May 24, 2019

(86) PCT No.: PCT/JP2019/020668
§ 371 (c)(1),
(2) Date: Apr. 21, 2021

(87) PCT Pub. No.: WO2019/225741
PCT Pub. Date: Nov. 28, 2019

(65) Prior Publication Data
US 2021/0236502 A1    Aug. 5, 2021

(30) Foreign Application Priority Data
May 25, 2018   (JP) ................................. 2018100669

(51) Int. Cl.
*A61K 31/5377* (2006.01)
*A61P 13/12* (2006.01)

(52) U.S. Cl.
CPC .......... *A61K 31/5377* (2013.01); *A61P 13/12* (2018.01)

(58) Field of Classification Search
CPC .................................................. A61K 31/5377
USPC ........................................................ 514/234.5
See application file for complete search history.

(56) References Cited

U.S. PATENT DOCUMENTS

| | | | |
|---|---|---|---|
| 8,299,070 B2 | 10/2012 | Inoue et al. | |
| 2013/0116240 A1 | 5/2013 | Inoue et al. | |
| 2017/0267662 A1 | 9/2017 | Inoue et al. | |
| 2018/0362506 A1 | 12/2018 | Inoue et al. | |
| 2020/0255408 A1 | 8/2020 | Inoue et al. | |

FOREIGN PATENT DOCUMENTS

| | | |
|---|---|---|
| JP | 2007145786 | 6/2017 |
| WO | WO2011065402 | 6/2011 |
| WO | WO2019225740 | 11/2019 |
| WO | WO2019225768 | 11/2019 |

OTHER PUBLICATIONS

PCT International Search Report in International Appln. No. PCT/JP2019/020668, dated Jul. 16, 3 pages English Translation.

*Primary Examiner* — Raymond J Henley, III
(74) *Attorney, Agent, or Firm* — Fish & Richardson P.C.

(57) ABSTRACT

The present invention provides a therapeutic agent or prophylactic agent for nephrotic syndrome, containing N-[2-(6,6-dimethyl-4,5,6,7-tetrahydro-1H-indazol-3-yl)-1H-indol-6-yl]-N-methyl-(2S)-2-(morpholin-4-yl)propanamide or a pharmaceutically acceptable salt thereof.

8 Claims, 2 Drawing Sheets

THERAPEUTIC OR PREVENTING AGENT FOR NEPHROTIC SYNDROME INCLUDING INDOLE COMPOUND

CROSS-REFERENCE TO RELATED APPLICATIONS

This application is the U.S. National Stage of International Application No. PCT/JP2019/020668, filed on May 24, 2019, which claims the benefit of Japanese Application No. 2018-100669, filed on May 25, 2018. The contents of each of these applications are incorporated herein by reference in their entirety.

TECHNICAL FIELD

The present invention relates to a novel pharmaceutical use of N-[2-(6,6-dimethyl-4,5,6,7-tetrahydro-1H-indazol-3-yl)-1H-indol-6-yl]-N-methyl-(2S)-2-(morpholin-4-yl)propanamide (hereinafter to be referred to as Compound A) or a pharmaceutically acceptable salt thereof. More particularly, the present invention relates to a therapeutic agent or prophylactic agent for nephrotic syndrome, containing Compound A or a pharmaceutically acceptable salt thereof.

BACKGROUND ART

Nephrotic syndrome is a syndrome characterized by a large amount of urinary protein based on promoted protein permeability due to renal glomerular capillary disorder and hypoproteinemia associated therewith. Nephrotic syndrome is accompanied by various symptoms such as edema, renal dysfunction, dyslipidemia, coagulation/fibrinolysis abnormality, and immune disorder and the like caused by a large amount of urinary protein, hypoalbuminemia, hypoproteinemia.

Nephrotic syndrome is widely divided into primary nephrotic syndrome and secondary nephrotic syndrome derived from other causative diseases. The primary nephrotic syndrome is developed due to primary glomerulonephritis such as minimal change nephrotic syndrome (MCNS), focal segmental glomerulosclerosis (FSGS), membranous nephropathy (MN) or proliferative nephritis. The secondary nephrotic syndrome is developed due to autoimmune diseases, metabolic diseases, infections, allergy hypersensitive diseases, tumors, medicaments, hereditary diseases and the like (non-patent document 1).

As an animal model exhibiting nephrotic syndrome-like symptoms, an anti-glomerular basement membrane (GBM) antibody-induced nephritis model is known (non-patent document 2).

Compound A, N-[2-(6,6-dimethyl-4,5,6,7-tetrahydro-1H-indazol-3-yl)-1H-indol-6-yl]-N-methyl-(2S)-2-(morpholin-4-yl)propanamide, and a pharmaceutically acceptable salt thereof are described in patent document 1 and patent document 2. Patent document 1 describes that Compound A has an inducible T cell kinase (ITK) inhibitory activity and can be a medicament effective for the prophylaxis or treatment of diseases such as rheumatoid arthritis, inflammatory bowel disease and the like, suppression of rejection in transplantation, and the like. Patent document 2 describes the production methods of Compound A and a pharmaceutically acceptable salt thereof.

DOCUMENT LIST

Patent Documents patent document 1: WO 2011/065402
patent document 2: WO 2016/002918

Non-Patent Documents non-patent document 1: Seiichi Matsuo (Supervisor (2014)) Ministry of Health, Labour and Welfare research project to overcome refractory disease, progressive kidney disease research group (ed.): Evidence-based nephrotic syndrome treatment guidelines 2014. tokyo-igakusha, p1.

non-patent document 2: Kohda, T et al. High nephritogenicity of monoclonal antibodies belonging to IgG2a and IgG2b subclasses in rat anti-GBM nephritis. Kidney Int. July 2004, Vol. 66, Issue 1, pages 177-186.

SUMMARY OF INVENTION

Technical Problem

The problem to be solved by the present invention is provision of a therapeutic drug for nephrotic syndrome.

Solution to Problem

The present inventors found in an experiment using a disease animal model showing nephrotic syndrome-like symptoms that Compound A and a salt thereof significantly reduce severity of the disease. Based on this finding, the present inventors have found that Compound A and a pharmaceutically acceptable salt thereof can be medicaments effective for nephrotic syndrome, and completed the present invention.

That is, the present invention provides the following.

[1] A therapeutic agent or prophylaxis agent for nephrotic syndrome, comprising a compound represented by the following chemical structural formula:

or a pharmaceutically acceptable salt thereof.

[2] The therapeutic agent or prophylaxis agent of [1], wherein the nephrotic syndrome is primary nephrotic syndrome or secondary nephrotic syndrome.

[3] The therapeutic agent or prophylaxis agent of [1] or [2], wherein the nephrotic syndrome is at least one symptom of nephrotic syndrome selected from the group consisting of hypoalbuminemia, hypoproteinemia, dyslipidemia, immune disorder, edema and hypercholesterolemia.

[4] The therapeutic agent or prophylaxis agent of any of [1] to [3], wherein the pharmaceutically acceptable salt is monohydrochloride.

[5] A method for treating or preventing nephrotic syndrome, comprising administering a therapeutically effective amount of a compound represented by the following chemical structural formula:

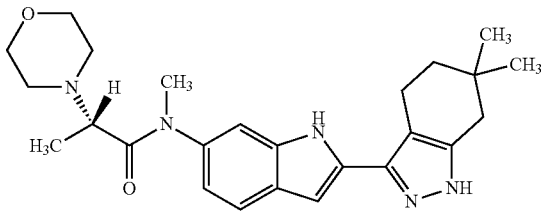 [SMILES: C[C@@H](C(=O)N(C)c1ccc2cc(-c3n[nH]c4c3CCC(C)(C)C4)[nH]c2c1)N1CCOCC1]

or a pharmaceutically acceptable salt thereof to a mammal.

[6] The method of [5], wherein the nephrotic syndrome is primary nephrotic syndrome or secondary nephrotic syndrome.

[7] The method of [5] or [6], wherein the nephrotic syndrome is at least one symptom of nephrotic syndrome selected from the group consisting of hypoalbuminemia, hypoproteinemia, dyslipidemia, immune disorder, edema and hypercholesterolemia.

[8] The method of any of [5] to [7], wherein the pharmaceutically acceptable salt is monohydrochloride.

[9] A compound represented by the following chemical structural formula:

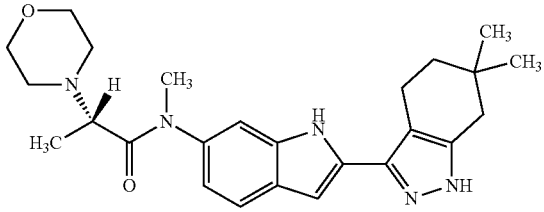 [SMILES: C[C@@H](C(=O)N(C)c1ccc2cc(-c3n[nH]c4c3CCC(C)(C)C4)[nH]c2c1)N1CCOCC1]

or a pharmaceutically acceptable salt thereof for use in treating or preventing nephrotic syndrome.

[10] The compound or a pharmaceutically acceptable salt thereof of [9], wherein the nephrotic syndrome is primary nephrotic syndrome or secondary nephrotic syndrome.

[11] The compound or a pharmaceutically acceptable salt thereof of [9] or [10], wherein the nephrotic syndrome is at least one symptom of nephrotic syndrome selected from the group consisting of hypoalbuminemia, hypoproteinemia, dyslipidemia, immune disorder, edema and hypercholesterolemia.

[12] The compound or a pharmaceutically acceptable salt thereof of any of [9] to [11], wherein the pharmaceutically acceptable salt is monohydrochloride.

[13] Use of a compound represented by the following chemical structural formula:

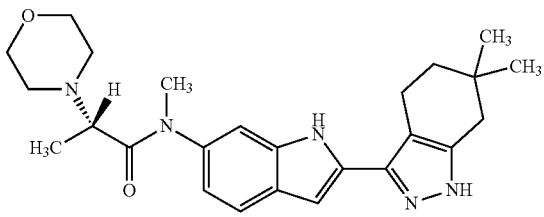 [SMILES: C[C@@H](C(=O)N(C)c1ccc2cc(-c3n[nH]c4c3CCC(C)(C)C4)[nH]c2c1)N1CCOCC1]

or a pharmaceutically acceptable salt thereof in producing a therapeutic agent or prophylactic agent for nephrotic syndrome.

[14] The use of [13], wherein the nephrotic syndrome is primary nephrotic syndrome or secondary nephrotic syndrome.

[15] The use of [13] or [14], wherein the nephrotic syndrome is at least one symptom of nephrotic syndrome selected from the group consisting of hypoalbuminemia, hypoproteinemia, dyslipidemia, immune disorder, edema and hypercholesterolemia.

[16] The use of any of [13] to [15], wherein the pharmaceutically acceptable salt is monohydrochloride.

Advantageous Effects of Invention

The present invention provides Compound A or a pharmaceutically acceptable salt thereof effective as a therapeutic agent for nephrotic syndrome.

DESCRIPTION OF EMBODIMENTS

Figure 1:
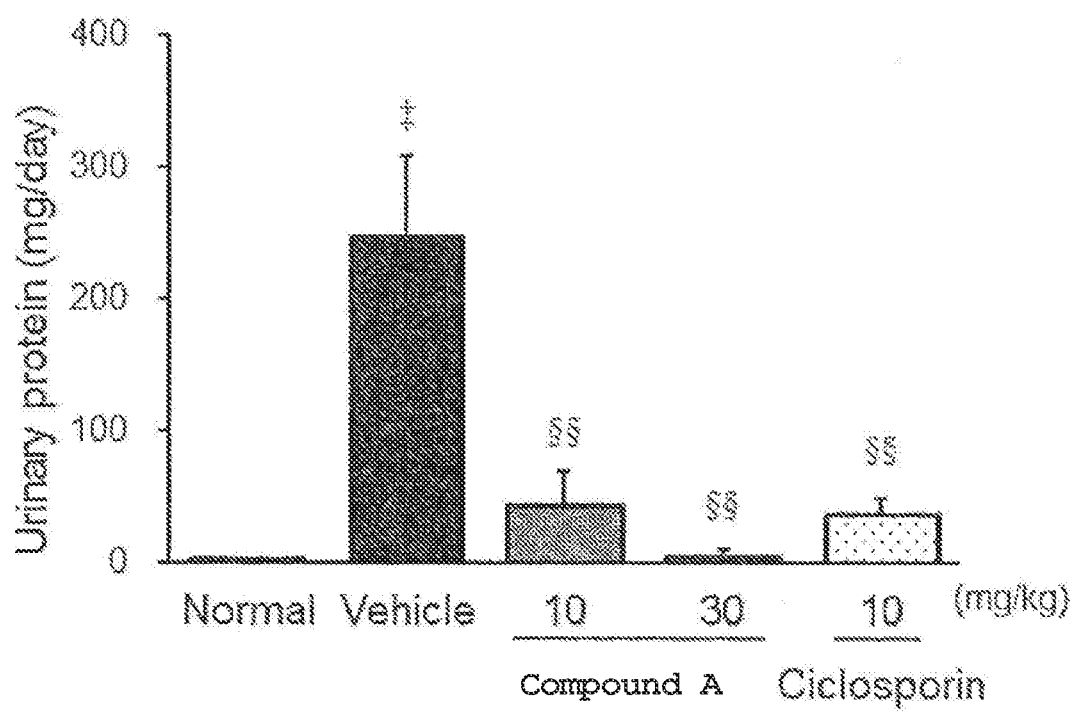
FIG. 1 shows urinary protein excretion levels of anti-GBM antibody induced nephritis model rats orally administered with a vehicle, monohydrochloride of Compound A, or Ciclosporin, and a normal rat orally administered with the vehicle.

The definitions of the terms in this specification are as follows.

Compound A is N-[2-(6,6-dimethyl-4,5,6,7-tetrahydro-1H-indazol-3-yl)-1H-indol-6-yl]-N-methyl-(2S)-2-(morpholin-4-yl)propanamide, and is represented by the following chemical structural formula:

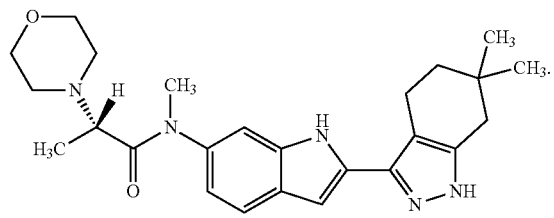 [SMILES: C[C@@H](C(=O)N(C)c1ccc2cc(-c3n[nH]c4c3CCC(C)(C)C4)[nH]c2c1)N1CCOCC1]

Any salt known in the technical field is acceptable as a "pharmaceutically acceptable salt" as long as it is not accompanied by excessive toxicity. Specifically, salts with inorganic acids, salts with organic acids, salts with inorganic bases, and salts with organic bases can be given as examples.

Various forms of pharmaceutically acceptable salt are well known in the field, for example, and are described in the references below, (a) Berge et al, J. Pharm. Sci., 66, p 1-19 (1977),
(b) Stahl et al, "Handbook of Pharmaceutical Salts: Properties, Selection, and Use" (Wiley-VCH, Weinheim, Germany, 2002), and
(c) Paulekuhn et al, J. Med. Chem., 50, p 6665-6672 (2007).

It is possible to obtain the respective pharmaceutically acceptable salts of Compound A by reacting Compound A with an inorganic acid, an organic acid, an inorganic base, or an organic base according to a method known per se. A pharmaceutically acceptable salt of Compound A may be formed as a half molecule, one molecule or two or more molecules of an acid or base with respect to one molecule of Compound A.

Salts with hydrofluoric acid, hydrochloric acid, hydrobromic acid, hydriodic acid, nitric acid, phosphoric acid, or sulfuric acid are given as examples of salts with inorganic acids.

Salts with acetic acid, adipic acid, alginic acid, 4-aminosalicylic acid, anhydromethylene citric acid, benzoic acid, benzenesulfonic acid, calcium edetate, camphoric acid, camphor-10-sulfonic acid, carbonic acid, citric acid, edetic acid, 1,2-ethanedisulfonic acid, dodecyl sulfate, ethane sulfonic acid, fumaric acid, glucoheptonic acid, gluconic acid, glucuronic acid, glycollylarsanilic acid, hexylresorcinic acid, hydroxy-naphthoic acid, 2-hydroxy-1-ethanesulfonic acid, lactic acid, lactobionic acid, malic acid, maleic acid, mandelic acid, methanesulfonic acid, methylsulfuric acid, methylnitric acid, methylenebis (salicylic acid), galactaric acid, naphthalene-2-sulfonic acid, 2-naphthoic acid, 1,5-naphthalenedisulfonic acid, oleic acid, oxalic acid, pamoic acid, pantothenic acid, pectic acid, picric acid, propionic acid, polygalacturonic acid, salicylic acid, stearic acid, succinic acid, tannic acid, tartaric acid, teoclic acid, thiocyanic acid, trifluoroacetic acid, p-toluenesulfonic acid, undecanoic acid, asparagine acid, or glutamic acid are given as examples of salts with organic acids.

Salts with lithium, sodium, potassium, magnesium, calcium, barium, aluminum, zinc, bismuth, or ammonium are given as examples of salts with inorganic bases.

Salts with arecoline, betaine, choline, clemizole, ethylenediamine, N-methylglucamine, N-benzylphenethylamine, tris(hydroxymethyl)methylamine, arginine, or lysine are given as examples of salts with organic bases.

Preferred embodiments of a "pharmaceutically acceptable salt" are as follows.

Salts with hydrochloric acid, nitric acid, sulfuric acid, phosphoric acid, or hydrobromic acid are given as examples of salts with inorganic acids.

Salts with oxalic acid, maleic acid, citric acid, fumaric acid, lactic acid, malic acid, succinic acid, tartaric acid, acetic acid, trifluoroacetic acid, benzoic acid, glucuronic acid, oleic acid, pamoic acid, methanesulfonic acid, benzenesulfonic acid, p-toluenesulfonic acid, or 2-hydroxy-1-ethanesulfonic acid are given as examples of salts with organic acids.

Salts with sodium, potassium, calcium, magnesium, or zinc are given as examples of salts with inorganic bases.

Salts with tris(hydroxymethyl)methylamine, N-methylglucamine, or lysine are given as examples of salts with organic bases.

A preferable pharmaceutically acceptable salt of Compound A among these is a monohydrochloride of Compound A represented by the following chemical structural formula:

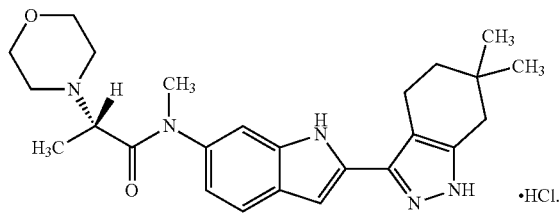 [SMILES: C[C@@H](C(=O)N(C)c1ccc2cc(-c3n[nH]c4c3CCC(C)(C)C4)[nH]c2c1)N1CCOCC1]

·HCl.

Compound A and the pharmaceutically acceptable salts thereof can be produced using a known method, a method described in patent document 1 or patent document 2, for example.

Compound A or the pharmaceutically acceptable salts thereof may exist as a solvate.

A "solvate" has a molecule of a solvent coordinated to Compound A or a pharmaceutically acceptable salt thereof, and this encompasses a hydrate. A pharmaceutically acceptable solvate is preferable as a solvate, and examples include a hydrate, an ethanol solvate, or a dimethyl sulfoxide solvate of Compound A or a pharmaceutically acceptable salt thereof.

Specifically, a hemihydrate, monohydrate, dihydrate, or mono(ethanol) solvate of Compound A, or a monohydrate of a sodium salt or a ⅔(ethanol) solvate of a dihydrochloride of Compound A can be given as examples. These solvates can be obtained according to known methods.

Compound A or a pharmaceutically acceptable salt thereof, each of which has been substantially purified, is preferable as Compound A or a pharmaceutically acceptable salt thereof. More preferably, Compound A or a pharmaceutically acceptable salt thereof has been purified to a purity of at least 80%.

The therapeutic agent or prophylactic agent for nephrotic syndrome of the present invention is produced, for example, according to a known method in the technical field of medicinal preparations by mixing Compound A or a pharmaceutically acceptable salt thereof with a suitable amount of at least one kind of pharmaceutically acceptable carrier or the like as appropriate. The amount of Compound A or a pharmaceutically acceptable salt thereof in said preparation differs according so to the dosage form, dose, and the like, but is, for example, 0.1 to 100 wt % of the entire preparation.

The therapeutic agent or prophylactic agent of the present invention can be administered orally or parenterally. Oral administration or parenteral administration such as intravenous, intramuscular, subcutaneous, percutaneous, local, or rectal administration can be given as examples of dosage forms. Tablets, capsules, granules, powders, troches, syrups, emulsions, suspensions, and the like can be given as examples of dosage forms that are appropriate for oral administration, and external preparations, suppositories, injections, eye drops, eye ointments, patches, gels, implants, nasal preparations, or pulmonary preparations can be given as examples of dosage forms that are appropriate for parenteral administration. These can be prepared according to known methods in the technical field of medicinal preparations.

Examples of a "pharmaceutically acceptable carrier" include various organic or inorganic carrier substances conventionally used as formulation materials, and examples include excipients, disintegrants, binders, fluidizers, lubricants, and the like for solid preparations; solvents, solubilizing agents, suspending agents, isotonicity agents, buffering agents, soothing agents, and the like for liquid preparations; and bases, emulsifiers, humectants, stabilizers, stabilizing agents, dispersants, plasticizers, pH regulators, absorption promoters, gelling agents, antiseptics, fillers, solvents, solubilizing agents, suspending agents, and the like for semisolid preparations. It is also acceptable to use additives such as preservatives, antioxidants, colorants, sweetening agents, and the like as necessary.

Examples of the "excipient" include lactose, sucrose, D-mannitol, D-sorbitol, cornstarch, dextrin, microcrystalline cellulose, crystalline cellulose, carmellose, carmellose calcium, sodium carboxymethyl starch, low-substituted hydroxypropylcellulose, gum arabic and the like.

Examples of the "disintegrant" include carmellose, carmellose calcium, carmellose sodium, sodium carboxymethyl starch, croscarmellose sodium, crospovidone, low-substituted hydroxypropylcellulose, hydroxypropylmethylcellulose, crystalline cellulose and the like.

Examples of the "binder" include hydroxypropylcellulose, hydroxypropylmethylcellulose, povidone, crystalline cellulose, sucrose, dextrin, starch, gelatin, carmellose sodium, gum arabic and the like.

Examples of the "fluidizer" include light anhydrous silicic acid, magnesium stearate and the like.

Examples of the "lubricant" include magnesium stearate, calcium stearate, talc and the like.

Examples of the "solvent" include purified water, ethanol, propylene glycol, macrogol, sesame oil, corn oil, olive oil and the like.

Examples of the "solubilizing agent" include propylene glycol, D-mannitol, benzyl benzoate, ethanol, triethanolamine, sodium carbonate, sodium citrate and the like.

Examples of the "suspending agent" include benzalkonium chloride, carmellose, hydroxypropylcellulose, propylene glycol, povidone, methylcellulose, glycerol monostearate and the like.

Examples of the "isotonicity agent" include glucose, D-sorbitol, sodium chloride, D-mannitol and the like.

Examples of the "buffering agent" include sodium hydrogenphosphate, sodium acetate, sodium carbonate, sodium citrate and the like.

Examples of the "soothing agent" include benzyl alcohol and the like.

Examples of a "base" include water, animal and vegetable oils (olive oil, corn oil, peanut oil, sesame oil, castor oil, and the like), lower alcohols (ethanol, propanol, propylene glycol, 1,3-butylene glycol, phenol, and the like), higher fatty acids and esters thereof, waxes, higher alcohols, polyhydric alcohols, hydrocarbons (white petrolatum, liquid paraffin, paraffin, and the like), hydrophilic petrolatum, purified lanolin, absorptive ointments, hydrous lanolin, hydrophilic ointments, starches, pullulan, gum arabic, tragacanth gum, gelatins, dextran, cellulose derivatives (methyl cellulose, carboxymethyl cellulose, hydroxyethyl cellulose, hydroxypropyl cellulose, and the like), synthetic polymers (carboxyvinyl polymer, sodium polyacrylate, poly(vinyl alcohol), polyvinyl pyrrolidone, and the like), propylene glycol, macrogol (Macrogol 200-600 and the like), and a combination of two or more kinds of these.

Examples of the "preservative" include ethyl paraoxybenzoate, chlorobutanol, benzyl alcohol, sodium dehydroacetate, sorbic acid and the like.

Examples of the "antioxidant" include sodium sulfite, ascorbic acid and the like.

Examples of the "colorant" include food colors (e.g., Food Color Red No. 2 or 3, Food Color Yellow No. 4 or 5 etc.), β-carotene and the like.

Examples of the "sweetening agent" include saccharin sodium, dipotassium glycyrrhizinate, aspartame and the like.

The dose of therapeutic agent or prophylactic agent of the present invention in mammal inclusive of human (e.g., human, mouse, rat, hamster, guinea pig, rabbit, cat, dog, swine, bovine, horse, sheep, monkey etc.) varies depending on the subject of administration, disease, symptom, dosage form, administration route and the like. For example, the daily dose for oral administration to a human adult patient (body weight: about 60 kg) is generally 0.1 mg-1 g, preferably 10 mg-800 mg, more preferably 30-300 mg, particularly preferably 50-200 mg, when calculated using Compound A as the active ingredient, and this amount can be administered in one to several portions per day either before a meal, after a meal, or during a meal. The duration of administration is not particularly limited.

Compound A or a pharmaceutically acceptable salt thereof can be used as an active ingredient of a therapeutic agent or prophylactic agent for nephrotic syndrome.

Nephrotic syndrome is generally diagnosed when the results of urinalysis and blood tests are as follows.

1. Urine protein 3.5 g or more per day (qualitative 4+)
2. Blood albumin concentration is 3.0 g/dl or less It may also accompany edema and hypercholesterolemia.

In this specification, "therapy" includes the improvement of symptoms, the prevention or delay of an increase in severity, the maintenance of remission, the prevention of exacerbation, and moreover, the prevention of relapse.

In the present specification, the "prophylaxis" means suppression of the onset of symptoms.

Nephrotic syndrome is classified into primary nephrotic syndrome and secondary nephrotic syndrome depending on the disease to be the causes thereof.

The primary nephrotic syndrome is caused by primary glomerulonephritis such as minimal change nephrotic syndrome (MCNS), focal segmental glomerulosclerosis (FSGS), membranous nephropathy (MN), proliferative nephritis or the like.

The secondary nephrotic syndrome is caused by, for example, autoimmune diseases, metabolic diseases, infections, allergic diseases, hypersensitive disease, tumors, medicaments, hereditary diseases and the like.

Compound A or a pharmaceutically acceptable salt thereof can be used for the treatment or prophylaxis of symptoms of nephrotic syndrome such as hypoalbuminemia, hypoproteinemia, dyslipidemia, immune disorder, edema, hypercholesterolemia and the like.

The pharmaceutical composition of the present invention can be used in combination with one or a plurality of other medicaments (hereinafter to be also referred to as a concomitant drug) according to a method generally employed in the medical field (hereinafter to be referred to as combination use).

The timing of administration of a drug containing Compound A or a pharmaceutically acceptable salt thereof and a concomitant drug is not limited. It is acceptable to administer these to an administration subject as a combination drug, and it is also acceptable to administer the two formulations either simultaneously or at a fixed interval. Furthermore, it is also acceptable to use the therapeutic agent or prophylactic agent of the present invention and a concomitant drug as a medication that is characterized in that the medication is a kit containing the present invention pharmaceutical composition and a concomitant drug. The dosage of a concomitant drug is acceptable as long as it is based on a dosage used in clinical practice, and the dosage can be appropriately selected according to the administration subject, disease, symptoms, dosage form, administration route, administration time, combination, and so on. The dosage form of a concomitant drug is not particularly limited, and is acceptable as long as a drug containing Compound A or a pharmaceutically acceptable salt thereof is combined with the concomitant drug. Examples of the concomitant drug include adrenal cortical steroid, cyclosporine, tacrolimus, cyclophosphamide, mizoribine, rituximab and the like.

One embodiment of the present invention provides a method so for treating or preventing nephrotic syndrome, including administering a therapeutically effective amount of Compound A or a pharmaceutically acceptable salt thereof to a mammal. Definitions and the like are as described above.

In this specification, an "effective amount" means, for example, the amount of a medication or drug that elicits a biological or medical response in a tissue, system, animal or human. Furthermore, a "therapeutically effective amount" means an arbitrary amount that either provides a treatment, cure, prophylaxis, or improvement where disease, disorder or side effect is improved or the rate of progression of disease is decreased, in comparison with a corresponding subject that has not received such an amount.

One embodiment of the present invention provides a pharmaceutical composition for treating or preventing nephrotic syndrome, which contains Compound A or a pharmaceutically acceptable salt thereof. Definitions and the like are as described above.

One embodiment of the present invention provides use of Compound A or a pharmaceutically acceptable salt thereof in producing a therapeutic agent or prophylactic agent for nephrotic syndrome. Definitions and the like are as described above.

One embodiment of the present invention provides Compound A or a pharmaceutically acceptable salt thereof for use in treating or preventing nephrotic syndrome. Definitions and the like are as described above.

EXAMPLE

The present invention will be explained below in detail using examples of embodiment, but the present invention is not so limited by these examples of embodiment.

Formulation examples of the present invention include the following formulations. The present invention is not, however, limited by these formulation examples.

Formulation Example 1: Production of Capsule 1) monohydrochloride of Compound A 30 mg
2) crystalline cellulose 10 mg
3) lactose 19 mg
4) magnesium stearate 1 mg
1), 2), 3) and 4) are mixed and filled in a gelatin capsule.

Formulation Example 2: Production of Tablet 1) monohydrochloride of Compound A 10 g
2) lactose 50 g
3) cornstarch 15 g
4) carmellose calcium 44 g
5) magnesium stearate 1 g
The entire amounts of 1), 2) and 3) and 30 g of 4) are kneaded with water, vacuum dried and sieved. The sieved powder is mixed with 14 g of 4) and 1 g of 5), and the mixture is tableted by a tableting machine. In this way, 1000 tablets each containing 10 mg of the monohydrochloride of Compound A per tablet are obtained.

Experimental Example 1: Suppressive Effect of Oral Administration of Compound A on an Increase in Urinary Protein Excretion and Plasma Total Cholesterol Concentration in Rat Anti-Glomerular Basement Membrane (GBM) Antibody Induced Nephritis Model Using a rat anti-GBM antibody induced nephritis model, the suppressive effect of Compound A on an increase in urinary protein excretion and plasma total cholesterol concentration so was evaluated. The evaluation was performed by reference to non-patent document 2. As the experiment animal, 8-week-old female WKY/NCrlCrlj rat (CHARLES RIVER LABORATORIES JAPAN, INC.) was used. Monohydrochloride of Compound A was dissolved in 0.5% (w/v) methylcellulose (MC) to prepare 2 mg/mL and 6 mg/mL Compound A solutions. Ciclosporin (Wako Pure Chemical Industries, Ltd., 0.5% (w/v)) was suspended in MC to prepare a 2 mg/mL Ciclosporin suspension.

To the vehicle group, Compound A administration group and Ciclosporin administration group, 60 µg/mL Nephritogenic Monoclonal Antibody (Chondrex) was intravenously administered at a volume of 0.5 mL/head (day 1). Then, 0.5% (w/v) methylcellulose (MC) was orally administered to normal group and vehicle group, 2 mg/mL or 6 mg/mL Compound A solution was orally administered to Compound A administration group, and 2 mg/mL Ciclosporin suspension was orally administered to Ciclosporin administration group, each at a volume of 5 mL/kg once per day for 17 days (days 1-17). 24 hr urine samples were collected (days 17-18) and blood samples were collected (day 18).

As for urine, the urine volume was measured, after which the protein concentration in the centrifugal supernatant was measured by absorbance at wavelength 600 nm/sub-wavelength 660 nm using a total protein assay kit (micro TP-Test Wako, Wako Pure Chemical Industries, Ltd.). The urinary protein excretion (mg/day) was calculated from the urine volume and the protein concentration.

As for blood, the total cholesterol concentration (mg/dL) in plasma obtained by centrifugation was measured using a biochemical automatic analysis apparatus (Hitachi automatic analysis apparatus 7180, Hitachi High-Technologies).

Figure 2:
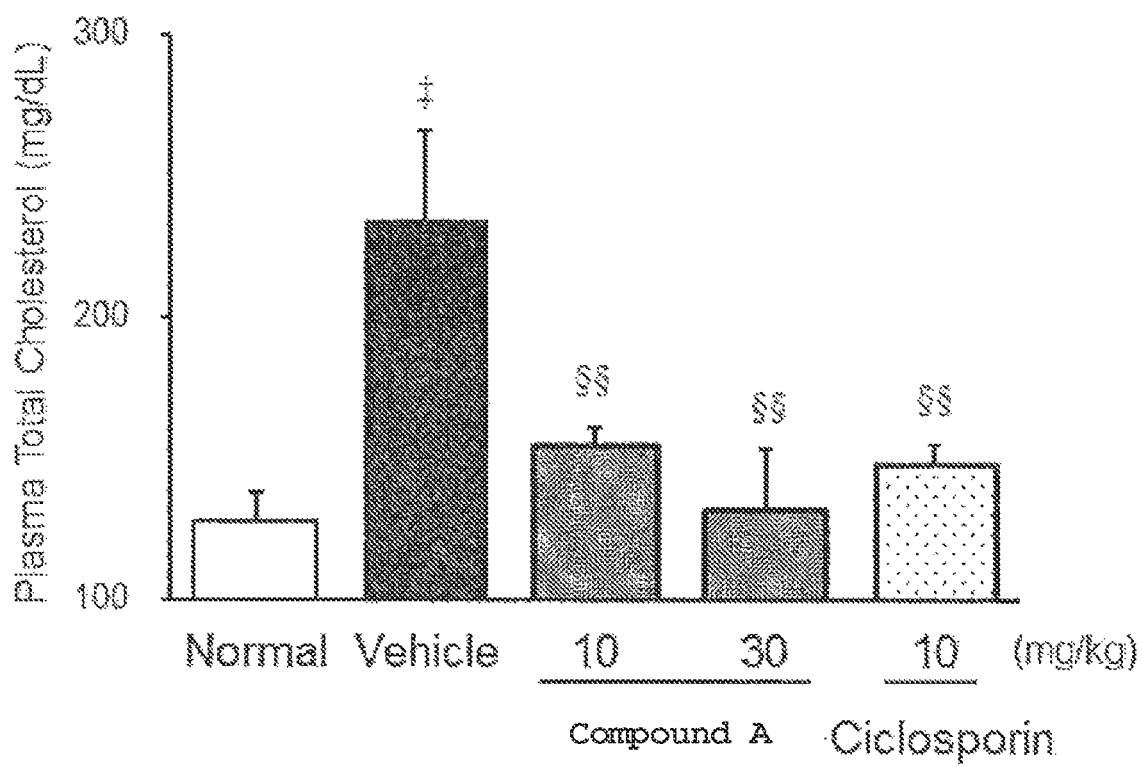
FIG. 2 shows plasma total cholesterol concentrations of anti-GBM antibody induced nephritis model rats orally administered with a vehicle, monohydrochloride of Compound A, or Ciclosporin, and a normal rat orally administered with the vehicle.

The mean of the urinary protein excretion and the plasma total cholesterol concentration was calculated. The results thereof are respectively shown in FIG. 1 and FIG. 2.

INDUSTRIAL APPLICABILITY

The present invention provides a novel pharmaceutical use of Compound A or a pharmaceutically acceptable salt thereof wherein the target disease is nephrotic syndrome.

The invention claimed is:
1. A method for treating nephrotic syndrome in a human subject in need thereof, comprising administering to the human subject a therapeutically effective amount of a compound represented by the following chemical structural formula:

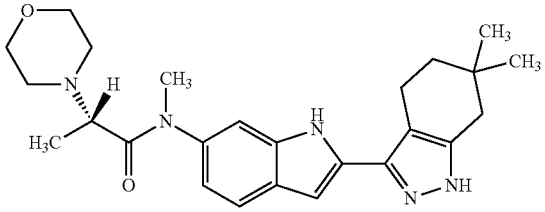 [SMILES: C[C@@H](C(=O)N(C)c1ccc2cc(-c3n[nH]c4c3CCC(C)(C)C4)[nH]c2c1)N1CCOCC1]

or a pharmaceutically acceptable salt thereof.
2. The method according to claim 1, wherein the nephrotic syndrome is primary nephrotic syndrome or secondary nephrotic syndrome.
3. The method according to claim 1, wherein the nephrotic syndrome is at least one symptom of nephrotic syndrome selected from the group consisting of hypoalbuminemia, hypoproteinemia, dyslipidemia, immune disorder, edema and hypercholesterolemia.

4. The method according to claim 1, wherein the pharmaceutically acceptable salt is monohydrochloride.

5. A method for preventing nephrotic syndrome in a human subject in need thereof, comprising administering to the human subject a therapeutically effective amount of a compound represented by the following chemical structural formula:

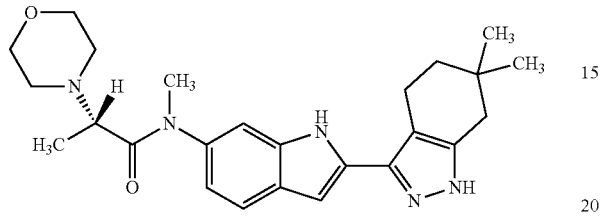

or a pharmaceutically acceptable salt thereof.

6. The method according to claim 5, wherein the nephrotic syndrome is primary nephrotic syndrome or secondary nephrotic syndrome.

7. The method according to claim 5, wherein the nephrotic syndrome is at least one symptom of nephrotic syndrome selected from the group consisting of hypoalbuminemia, hypoproteinemia, dyslipidemia, immune disorder, edema and hypercholesterolemia.

8. The method according to claim 5, wherein the pharmaceutically acceptable salt is monohydrochloride.

* * * * *